(12) United States Patent
Su et al.

(10) Patent No.: US 8,712,704 B2
(45) Date of Patent: Apr. 29, 2014

(54) DEFECT DETECTION SYSTEM AND METHOD

(75) Inventors: Jui-Yiao Su, Hsinchu (TW); Yu-Liang Chung, Hsinchu (TW); Chun-Chieh Wang, Hsinchu (TW); Chien-Feng Wu, Hsinchu (TW); Yan-Chen Liu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 383 days.

(21) Appl. No.: 12/879,215

(22) Filed: Sep. 10, 2010

(65) Prior Publication Data

US 2012/0016600 A1 Jan. 19, 2012

(30) Foreign Application Priority Data

Jul. 15, 2010 (TW) .............................. 99123238 A

(51) Int. Cl.
*G06F 19/00* (2011.01)
(52) U.S. Cl.
USPC ................... 702/36; 702/35; 702/56; 73/573; 73/583; 73/599; 73/659
(58) Field of Classification Search
USPC ........... 702/35–36, 56; 73/573, 583, 599, 659
See application file for complete search history.

(56) References Cited

U.S. PATENT DOCUMENTS

| 4,603,584 A | 8/1986 | Bartle et al. |
| 4,829,823 A * | 5/1989 | Michel ............................ 73/579 |
| 5,195,046 A * | 3/1993 | Gerardi et al. ................... 702/35 |
| 2005/0097961 A1* | 5/2005 | Yagi et al. ........................ 73/573 |
| 2006/0062403 A1 | 3/2006 | Yagi |

FOREIGN PATENT DOCUMENTS

| CN | 100405384 C | 7/2008 |
| EP | 1548430 A1 | 6/2005 |
| EP | 1630551 A1 | 3/2006 |
| JP | 2005142495 A | 6/2005 |
| JP | 2006064464 A | 3/2006 |
| JP | 2006090871 A | 4/2006 |
| TW | M346121 U | 12/2008 |
| TW | M350015 | 2/2009 |
| TW | 200912286 A | 3/2009 |
| TW | M353466 U | 3/2009 |

OTHER PUBLICATIONS

Norden E. Huang et al., "The empirical mode decomposition and the Hilbert spectrum for nonlinear and non-stationary time series analysis", Nonlinear and non-stationary time series analysis, pp. 903-995.

(Continued)

*Primary Examiner* — Jonathan C. Teixeira Moffat
*Assistant Examiner* — Hien Vo
(74) *Attorney, Agent, or Firm* — Rabin & Berdo, P.C.

(57) ABSTRACT

A defect detection system and method enable a fastened crystalline silicon product to generate micro-vibration by a micro-vibration excitation device, so as to enable the crystalline silicon product to generate an excitation signal, then to acquire the excitation signal by a acquisition device, so as to analyze the excitation signal acquired by the acquisition device in the time and frequency domain by an analysis detection device with a specific analysis, and to obtain an analysis result, at last, determine a defect state of the crystalline silicon product according to the analysis result.

18 Claims, 8 Drawing Sheets

(56) References Cited

OTHER PUBLICATIONS

Nanki Jitsukawa et al., "Time-frequency analysis of impact sound of composite materials", SICE 2002, pp. 1076-1079.

Gao Qun-qin et al., "Research on Time-frequency Characteristics of Engine Induction Noise and Time-frequency Representation of the Acoustic Signals", 2009 IEEE.

T.Y. Wu et al., "Looseness Diagnosis of Rotating Machinery Via Vibration Analysis Through Hilbert Huang Transform Approach", Journal of Vibration and Acoustics, Jun. 2010, vol. 132.

Hu et al., "Research on time-frequency analysis in non destructive testing for laminated composite material", Transducer and Microsystern Technologies, pp. 9-12, 2009.

Dallas et al., Resonance ultrasonic vibrations for crack detection in photovoltaic silicon wafers, Measurement Science and Technology, Feb. 5, 2007, vol. 18, pp. 852-858.

Taiwan Patent Office, Office Action, Patent Application Serial No. TW099123238, Aug. 16, 2013, Taiwan.

* cited by examiner

DEFECT DETECTION SYSTEM AND METHOD

TECHNICAL FIELD

This disclosure relates to a defect detection system and method, and particularly, to a system and method for performing fragmentation defect detection with respect to a crystalline silicon product by using a time-frequency analysis.

BACKGROUND

The most thing during detection procedure of crystalline silicon product process, for instance, solar panel process, is that rapidly and correctly detecting and excluding products having fragmentation defects, so as to maintain defective rate and reliability of products. Since the fragmentation defects are classified as naked-eyes-identifiable external fragmentation defects and naked-eyes-unidentifiable internal fragmentation defects, the detection procedure is generally focused on how to immediately detect products having internal fragmentation defects.

As disclosed in Taiwan Patent Issuance No. M350015, a device for inspecting defect of photovoltaic element is used to find out a fragmentation defect of a photovoltaic element, for instance a solar panel, through analyzing a spectrum of an acoustic signal in frequency domain excited from the photovoltaic element. The device enables the fragmentation defect of the photovoltaic element to excite the acoustic signal through a resonance manner; however, it is not easy to excite an internal fragmentation defect, which cannot be identified by naked eyes, and generate an acoustic signal through a resonance mode. Hence, in practice, such detection device is usually unable to find out whether or not a solar panel has an internal fragmentation defect. Furthermore, the detection device have to equipped with a database pre-storing a spectrum of a standard acoustic signal to perform subsequent analysis and inspection, so as to cause extra cost burden to an user. Moreover, the accuracy of an analysis result obtained by only analyzing the spectrum of the acoustic signal in frequency domain is often insufficiently low, and thus the result cannot efficiently identify a solar panel having external or internal fragmentation defects.

Additionally, an inspection technique is disclosed in U.S. Patents Publication No. 20050097961 A1 and 20060062403 A1. Specifically, an acoustic signal generated from a tested substrate, for instance, a solar panel, is analyzed in frequency domain, so as to identify a fragmentation defect of the solar panel by a spectrum of the acoustic signal in frequency domain. Nevertheless, since the above inspection technique enables the tested substrate to excite the acoustic signal through directly striking the tested substrate, damages following with improper operation would be contributed to the tested substrate. Furthermore, such inspection technique also has to be cooperated with a database pre-storing the spectrum of a standard acoustic signal, and thus will cause the extra burden to the user. In addition, the aforementioned inspection technique also only analyzes the spectrum of the acoustic signal in frequency domain, and thus cannot provide an analysis result with higher accuracy.

U.S. Pat. No. 4,603,584 discloses an inspection technique which is still limited to analyzes a spectrum of an acoustic signal in frequency domain. Hence, it still couldn't provide an analysis result with higher accuracy.

In this regard, there is a need to develop a defect detection system and method for detecting a crystalline product that can accurately detect not only naked-eyes-identifiable external fragmentation defects but also naked-eyes-unidentifiable internal fragmentation defects while neither contributing any improper damage to the tested crystalline product nor increasing user load.

SUMMARY

In view of the above-mentioned problems in the prior art, it is a primary objective of the disclosure to provide a defect detection system and method for simultaneously and accurately detecting naked-eyes-identifiable external fragmentation defects and naked-eyes-unidentifiable internal fragmentation defects.

To achieve the above-mentioned and other objectives, a defect detection system for detecting a crystalline silicon product is provided according to the disclosure. The defect detection system comprises a fastening device, a micro-vibration excitation device, a acquisition device, and an analysis detection device, wherein the fastening device is used for fastening the crystalline silicon product; the micro-vibration excitation device is used for enabling the crystalline silicon product fastened by the fastening device to generate micro-vibration, so as to enable the crystalline silicon product fastened by the fastening device to generate an excitation signal; the acquisition device is used for acquiring the excitation signal; and the analysis detection device is used for performing a time-frequency analysis with respect to the acquired excitation signal by a specific analysis, so as to generate an analysis result.

A defect detection method for detecting a crystalline silicon product is provided according to the disclosure. The defect detection method comprises the steps of: (a) enabling the crystalline silicon product to generate micro-vibration, so as to enable it to generate an excitation signal; (b) acquiring the excitation signal generated from the crystalline silicon product; and (c) performing a time-frequency analysis with respect to the acquired excitation signal by a specific analysis, so as to generate an analysis result.

In conclusion, the defect detection system and method in accordance with the disclosure enable the crystalline silicon product to generate the micro-vibration, so as to generate the excitation signal, then acquire the excitation signal, so as to perform the time-frequency analysis by the specific analysis with respect to the excitation signal, and further determine the defect state of the crystalline silicon product, such as defect size, defect position, defect quantity, and/or defect alignment, according to the analysis result. Thereby, the defect detection system and method not only can accurately detect external fragmentation defects and internal fragmentation defects of the crystalline silicon product, but also cause no improper damage to the tested crystalline silicon product and increase no extra cost burden to the user.

BRIEF DESCRIPTION OF THE DRAWINGS

The disclosure can be more fully understood by reading the following detailed description of the preferred embodiments, with reference made to the accompanying drawings, wherein.

DETAILED DESCRIPTION OF THE EMBODIMENTS

Figure 1A:
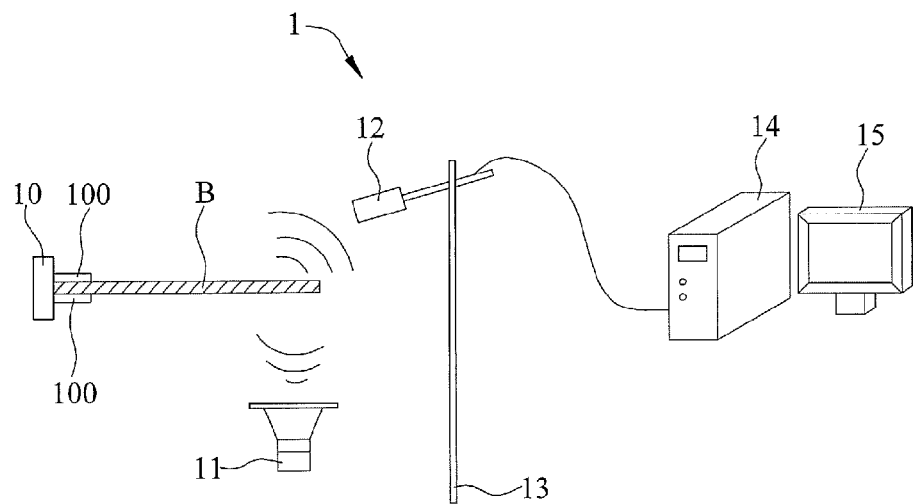
FIG. 1A is a schematic diagram of a fundamental architecture of a defect detection system in accordance with the disclosure.

The following illustrative embodiments are provided to illustrate the disclosure of the disclosure, these and other advantages and effects can be apparently understood by those in the art after reading the disclosure of this specification. The disclosure can also be performed or applied by other different embodiments. The details of the specification may be on the basis of different points and applications, and numerous modifications and variations can be devised without departing from the spirit of the disclosure.

FIGS. 1A, 1B, 1C, 1D, and 1E illustrate the fundamental architecture diagrams of a defect detection system in accordance with the disclosure. As illustrated, the defect detection system 1 comprises a fastening device 10, a micro-vibration excitation device 11, a acquisition device 12, an isolation device 13, an analysis detection device 14, a display device 15.

The fastening device 10 is used to fasten a crystalline silicon product B, such as a polycrystalline silicon thin substrate or a monocrystalline silicon thin substrate. In the present embodiments, the fastening device 10 has one or more clamping member 100 which may flexibly swing. The clamping member 100 holds an edge of the crystalline silicon product B, so as to achieve fixed effect. And the crystalline silicon product B may be a solar panel. In addition, the fastening device 10 may also be designed to a vacuum suction device with a suction member (not shown), as the embodiments shown in FIG. 1D and FIG. 1E, which is used to suck and fix the crystalline silicon product B. The clamping member 100 and the suction member may also be integrated according to users' requirements.

The micro-vibration excitation device 11 is used to enable the crystalline silicon product B hold by the fastening device 10 to generate micro-vibration, so as to enable the crystalline silicon product B to generate an excitation signal according to the micro-vibration. In the illustrative embodiment, the micro-vibration excitation 11 may be a contact impactor or a contactless pneumatic nozzle, an ultrasonic producer, and/or an acoustic resonator. Furthermore, output power of the micro-vibration excitation device 11 may be regulated according to a specification of the crystalline silicon product B; that is, the output power can be properly regulated according to structural features of the crystalline silicon product B to-be-tested to avoid, due to an excessive power, damages (e.g., fragments) to the crystalline silicon product B during a micro-vibration process. Even more, the micro-vibration excitation device 11 may also enable the crystalline silicon product B to generate more than once micro-vibration with different direction. And the excitation signal generated form the crystalline silicon product B is a micro-vibration signal, for instance, an acoustic signal.

Figure 1B:
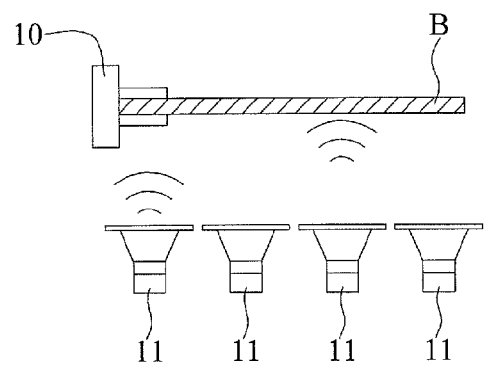
FIG. 1B is a partial schematic diagram of an illustrative embodiment of the system shown in FIG. 1A.
Figure 1C:
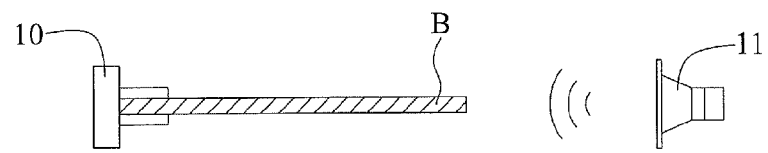
FIG. 1C is a partial schematic diagram of another illustrative embodiment of the system shown in FIG. 1A.
Figure 1D:
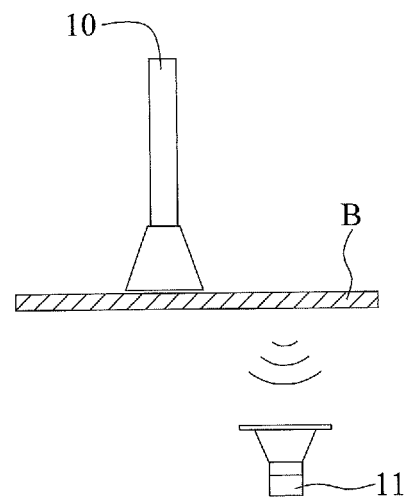
FIG. 1D is a partial schematic diagram of another illustrative embodiment of the system shown in FIG. 1A.
Figure 1E:
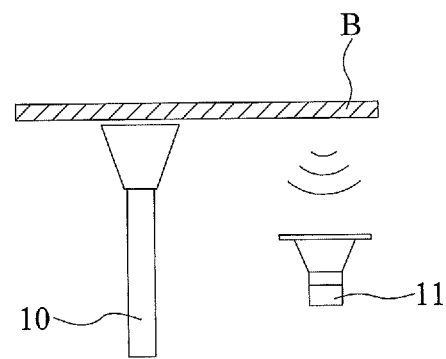
FIG. 1E is a partial schematic diagram of another illustrative embodiment of the system shown in FIG. 1A.

It is noteworthy that, an quantity, setting orientation, and actuating method of the micro-vibration excitation device 11 may all be altered according to different requirements. For example, as shown in FIGS. 1A, 1D, and 1E, only one micro-vibration excitation 11 is disposed at a vertical side of the crystalline silicon product B. As illustrated in FIG. 1C, only one micro-vibration excitation 11 may also be disposed at a horizontal side of the crystalline silicon product B. Certainly, as illustrated in FIG. 1B, a plurality of micro-vibration excitation 11 are disposed in array and actuated one by one.

The acquisition device 12 is used to acquire the excitation signal generated from the crystalline silicon product B by the micro-vibration excitation device 11. In the embodiment, the acquisition device 12 may be an industry-specific microphone or a sound level meter having related signal amplifier circuits and filtering circuits. Additionally, the acquisition device 12 may still have a recording function, thereby reappear all the micro-vibration signals generated from the crystalline silicon product B.

The isolation device 13 for separating the fastening device 10, the micro-vibration excitation device 11, and the acquisition device 12 from external environment is connected to the acquisition device 12, so as to enable the acquisition device 12 to acquire the excitation signal generated from the crystalline silicon product B under no interference or low interference environment. In the embodiment, the isolation device 13 isolates the fastening device 10, the micro-vibration excitation device 11, and the acquisition device 12, so as to achieve soundproof effect.

The analysis detection device 14 is used to perform a time-frequency analysis by a specific analysis with respect to the excitation signal acquired by the acquisition device 12, so as to generate analysis result in the time domain and the frequency domain with respect to the excitation signal. Further, a defect state of the crystalline silicon product B is determined by detecting the crystalline silicon product B according to the analysis result. In the present embodiment, the analysis detection device 14 may be a smart processing equipment having analysis calculating function and comprises a record module for recording the excitation signal acquired by the acquisition device 12, and/or the analysis result made by the analysis detection device 14 (not shown). Furthermore, in the present embodiment, the analysis detection device 14 performs an time-frequency analysis which collectively analyze the excitation signal in the time domain and the frequency domain acquired by the acquisition device 12 according to one or more of a short-time Fourier transform method, a continuous wavelet transform method, and a Hilbert-Huang transform approach, so as to obtain time-, frequency-, and energy-change results of the excitation signal. In this manner, the analysis detection device 14 may further characterize the time, frequency, and energy change results of the excitation signal and then analyze the characterized change results by an artificial intelligence algorithm, for instance, an artificial neural network and/or a support vector machine, so as to determine types of defect states of the crystalline silicon product B, such as the external fragmentation defects and internal fragmentation defects, or the size, position, quantity, and/or of the alignment defects with respect to the crystalline silicon product B.

The display device 15 is used to selectively display the analysis result generated by or the defect state determined by the analysis detection device 14. In the embodiment, the display device 15 is a liquid crystal screen.

It is noted that the defect detection system 1 in accordance with the disclosure may be selectively provided the isolation device 13 and the display device 15 according to the budget, demand, or the implementation environment for the user. In other words, the defect detection system 1 in accordance with the disclosure may operate by providing only the fastening device 10, the micro-vibration excitation device 11, the acquisition device 12, and the analysis detection device 14.

Figure 2A:
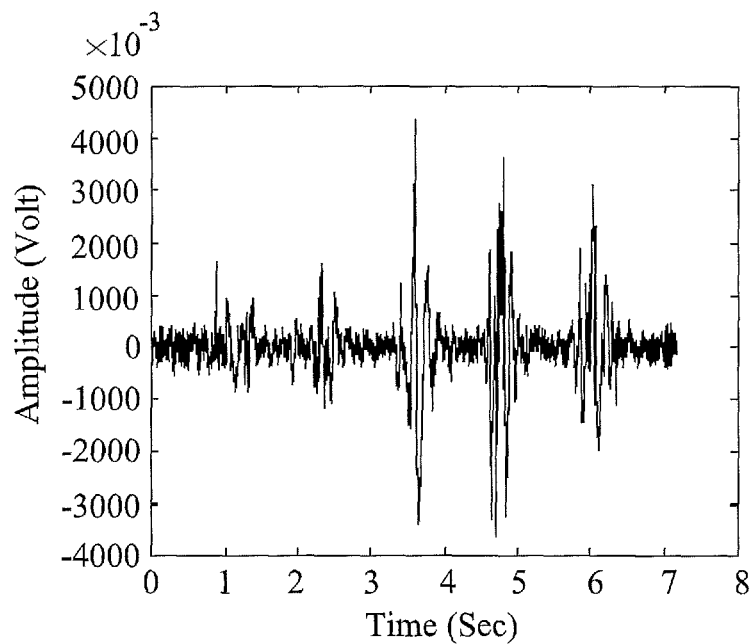
FIG. 2A to FIG. 2C respectively illustrate a typical time-domain signal diagram, a frequency-domain signal diagram, and a time-frequency signal energy distribution diagram of a crystalline silicon product having no fragmentation defect analyzed by an analysis detection device of the disclosure.
Figure 2B:
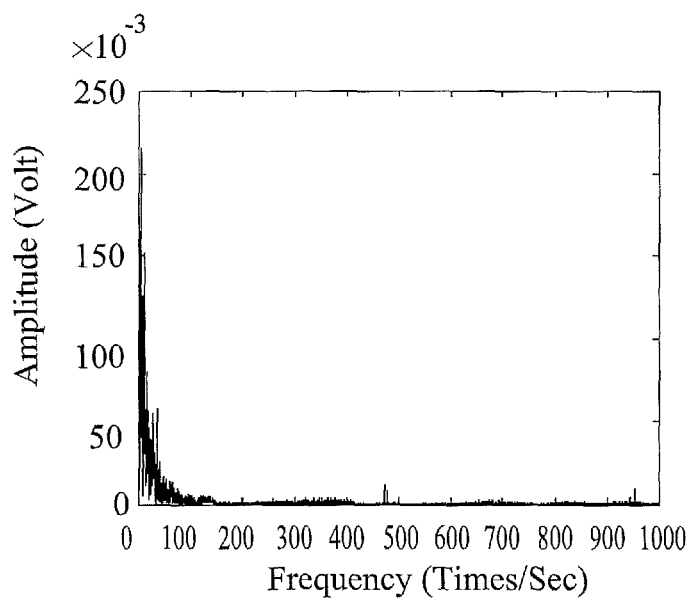
Figure 2C:
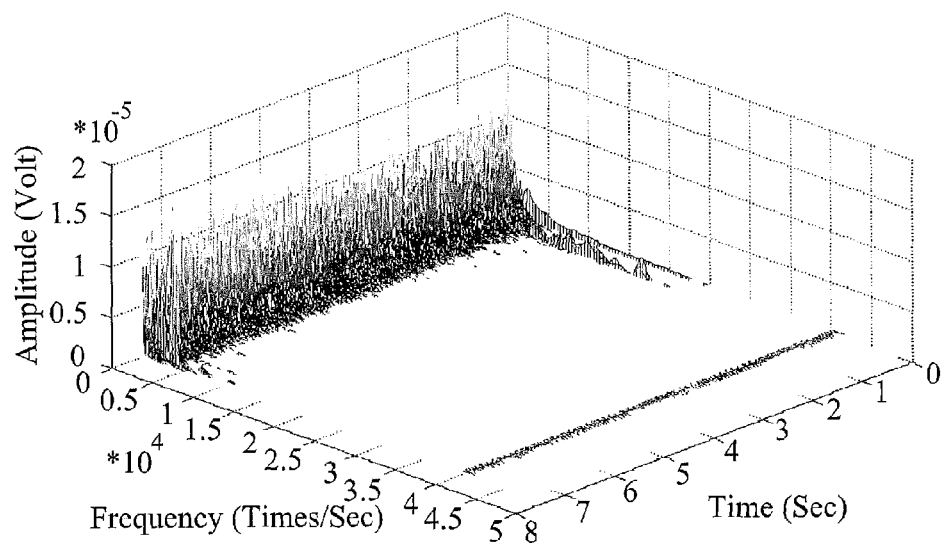
Figure 2D:
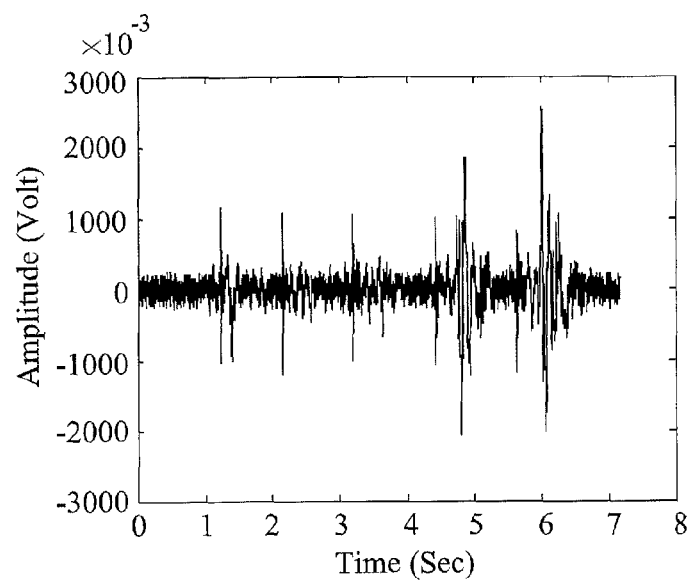
FIG. 2D to FIG. 2F respectively illustrate the typical time-domain signal diagram, the frequency-domain signal diagram, and the time-frequency signal energy distribution diagram of the crystalline silicon product having fragmentation defects analyzed by the analysis detection device of the disclosure.
Figure 2E:
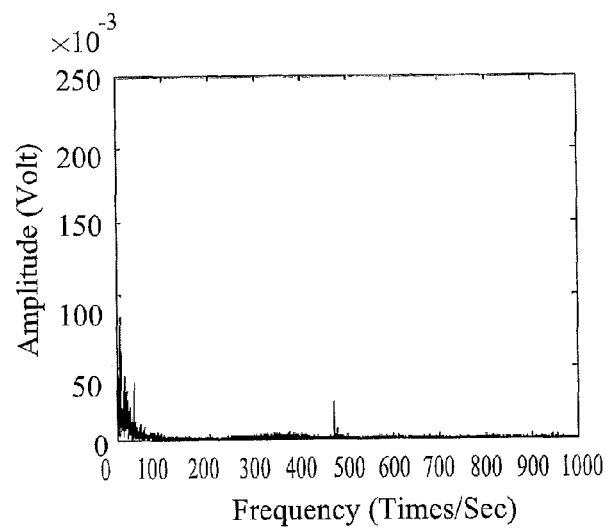
Figure 2F:
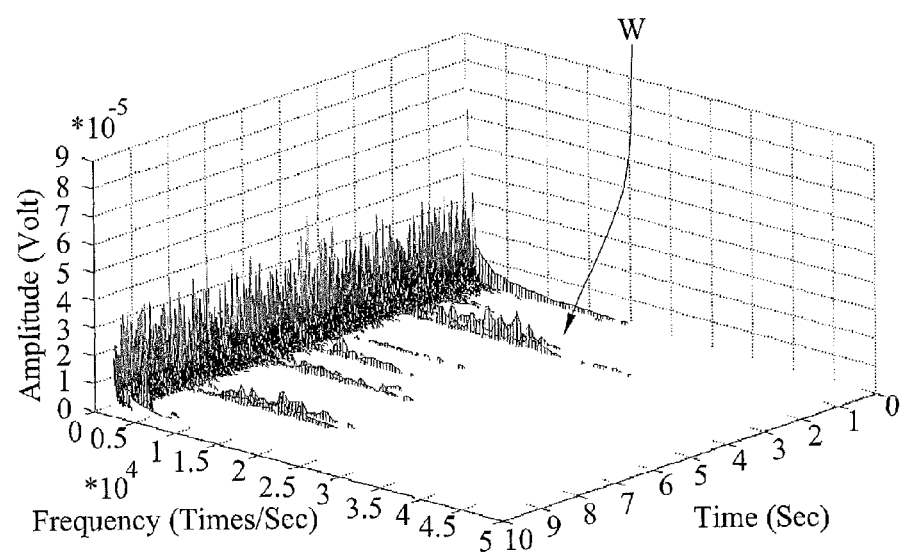

Referring to FIGS. 2A to 2F, the analysis and detection actuation of the analysis detection device 14 as described previously, can be clearly understood. FIG. 2A illustrates a typical time-domain signal diagram of the crystalline silicon product B having no fragmentation defect after analyzed by the analysis detection device 14; FIG. 2B illustrates a frequency-domain signal diagram; FIG. 2 C illustrates a time-frequency signal energy distribution diagram; FIG. 2D illustrates a typical time-domain signal diagram of the crystalline silicon product B having the fragmentation defects after analyzed by the analysis detection device 14; FIG. 2E illustrates a frequency-domain signal diagram; and FIG. 2F illustrates a time-frequency signal energy distribution diagram.

Assuming the crystalline silicon product B being with no fragmentation defects, the acquisition device 12 acquires the excitation signal provided for the analysis detection device 14 to perform analysis and calculation after the micro-vibration excitation device 11 enables the crystalline silicon product B to generate the excitation signal. At this time, the time-domain signal diagram and the frequency-domain signal diagram, as shown respectively in FIGS. 2A and 2B, are calculated from the analysis detection device 14. Then, the analysis detection device 14 collectively analyzes the time-domain signal diagram and the frequency-domain signal diagram by the short-time Fourier transform method, the continuous wavelet transform method, and/or the Hilbert-Huang transform approach, so as to obtain the time-frequency signal energy distribution diagram, as shown in FIG. 2C.

Moreover, assuming the crystalline silicon product B being with the fragmentation defects, the acquisition device 12 similarly acquires the excitation signal provided for the analysis detection device 14 to perform analysis and calculation after the micro-vibration excitation device 11 enables the crystalline silicon product B to generate the excitation signal. Further, the time-domain signal diagram and the frequency-domain signal diagram, as respectively shown in FIG. 2D and FIG. 2E, are calculated from the analysis detection device 14, and then the analysis detection device 14 performs a time-frequency analysis which collectively analyze the time-domain signal diagram and the frequency-domain signal diagram, by the short-time Fourier transform method, the continuous wavelet transform method, and/or the Hilbert-Huang transform approach, so as to obtain the time-frequency signal energy distribution diagram as shown in FIG. 2F.

In comparison of the time-frequency signal energy distribution diagram in FIG. 2C with that in FIG. 2F, one or more pulse surges W are observed after analyzing the time-frequency signal energy distribution diagram, (FIG. 2F) which is obtained by collectively analyzing the crystalline silicon product B having the fragmentation defects in time and frequency domain by the analysis detection device 14; and there will be no pulse surge W in the time-frequency signal energy distribution diagram (FIG. 2C) of the crystalline silicon product B having no fragmentation defect. Therefore, the analysis detection device 14 may determine whether or not the pulse surge W exists in the obtained time-frequency signal energy distribution diagram by using the artificial intelligence algorithm. Accordign, the defect state of the crystalline silicon product B can be detected on the result of the stermination as described above.

Figure 3:
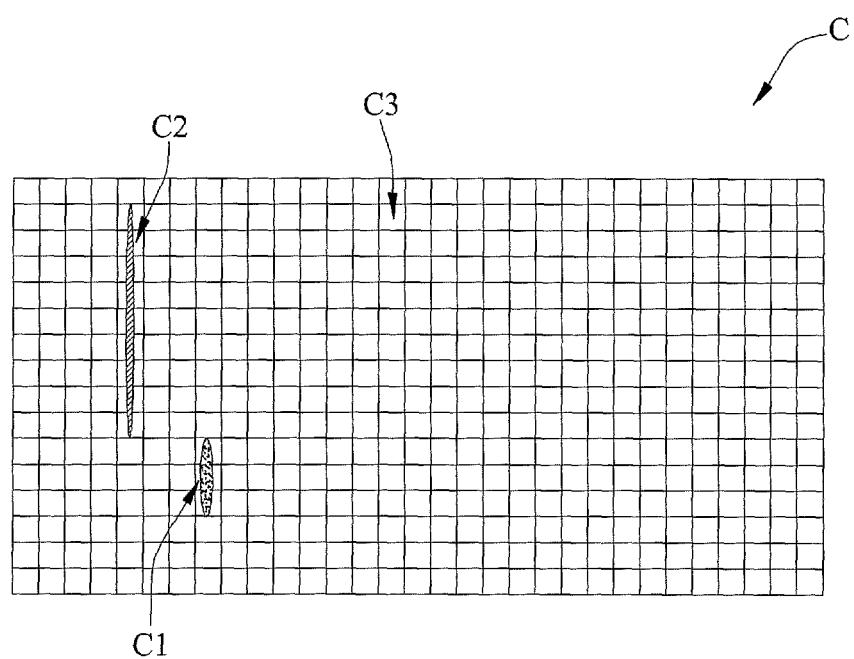
FIG. 3 is a typical energy grid diagram of the time-frequency signal energy distribution diagram of the crystalline silicon product having fragmentation defects characterized by the analysis detection device of the disclosure.

Specifically, the analysis detection device 14 can further characterize the time, frequency, and energy change results of the calculated excitation signal by a gridding method, and then analyze the characterized change results through the artificial intelligence algorithm, for instance, the artificial neural network and/or the support vector machine, so as to further increase detection accuracy and efficiency. For example, the time-frequency signal energy distribution diagram may be characterized as an energy grid diagram C, as shown in FIG. 3, by the analysis detection device 14 according to the gridding method. Since zones C1, C2 in the energy grid diagram C may represent energy concentration and a plurality of zones C3 in the energy grid diagram C may represent no energy concentration, the crystalline silicon product B is rapidly and accurately detected from the energy distribution situation of the energy grid diagram C as a product having the fragmentation defects by the analysis detection device 14 according to the artificial intelligence algorithm automatically. In addition, since the closeness level of the zones C1, C2 in the energy grid diagram C may represent energy quantification level, the fragmentation defect level of the product may be detected. The quantity of the zone C3 may be regulated according to predetermined resolution but not according to the numbers shown in the drawings.

Further, the quantity of the pulse surge W varies according to the number of times of the excitation signal generated from the crystalline silicon product B, and the number of times of the excitation signal depends on the number of times of the micro-vibration generated from the crystalline silicon product B enabled by the micro-vibration excitation device 11, that is, the quantity of the pulse surge W may vary according to the user settings of the micro-vibration excitation device 11, and the pulse surge W is a transient characteristic. In addition, it is known that, form contents of the frequency-domain signal diagrams as shown in FIG. 2B and FIG. 2E, no matter whether the crystalline silicon product B has fragmentation defects, the difference of the frequency-domain signals therebewteen is not obvious. As a result, the prior art cannot obtain an accuracy analysis result merely through analyzing an acoustic signal spectrum in frequency domain.

In practical implementation, whether or not the analysis detection device 14 effectively determines the defect state of the crystalline silicon product B, partially depends on whether or not the micro-vibration aligns with the texture direction of the fragmentation defects of the crystalline silicon product B, so as to enable the crystalline silicon product B having the fragmentation defects to generate the excitation signal. Under the circumstance, the defect detection system 1 of the disclosure may selectively further comprise a steering device (not shown) used to change direction of the fastening device 10. And the micro-vibration excitation device 11 can enable the crystalline silicon product B fastened by the fastening device 10 to generate plural times (e.g., five times) of micro-vibrations in a predetermined time (e.g., seven seconds). Accordingly, if the tested crystalline silicon product B is a product having fragmentation defects, the steering device synchronously changes direction of the fastening device 10 during the micro-vibration excitation device 11 enabling the crystalline silicon product B to generate plural times of micro-vibrations, so as to enable at least one texture direction of the plural times of the micro-vibrations to align with texture direction of the fragmentation defect, thereby to increase detection accuracy.

Figure 4A:
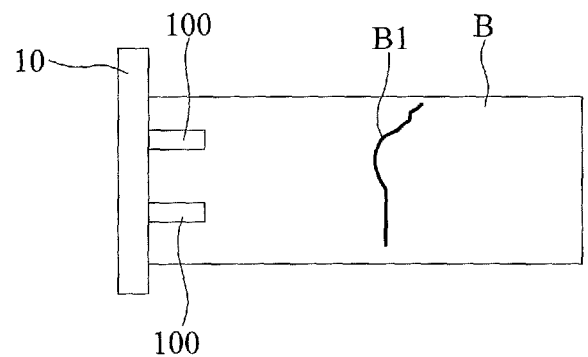
FIG. 4A is a top view of an aspect of an embodiment of the fastening device and the crystalline silicon product in FIG. 1.
Figure 4B:
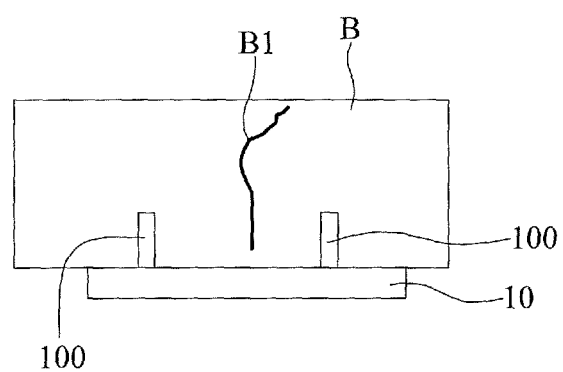
FIG. 4B is a top view of another aspect of an embodiment of the fastening device and the crystalline silicon product in FIG. 1.

Referring to FIGS. 1A, 4A, and 4B, aspects of direction change with respect to an embodiment of the fastening device 10 can be clearly understood. FIG. 4A illustrates a top view of the clamping member 100 of the fastening device 10 hold on a shorter side of the crystalline silicon product B, and FIG. 4B illustrates a top view of the clamping member 100 of the fastening device 10 hold on a longer side of the crystalline silicon product B.

As illustrated, the crystalline silicon product B has a internal crack B1 of which the texture direction tends to be parallel to the shorter side of the crystalline silicon product B. Therefore, the steering device may sequentially change the direction of the fastening device 10 during the micro-vibration excitation device 11 enabling the crystalline silicon product B to generate plural times of micro-vibrations, that is, enabling the clamping member 100 of the fastening device 10 to hold by turns the shorter side (FIG. 4A) and the longer side (FIG. 4B) of the crystalline silicon product B. As a result, at least one texture direction of the plural times of the micro-vibrations can be assumed to align with the texture direction of the internal crack B1.

It is noted that the steering device described previously is designed to change the direction of not only the fastening device 10 but also the micro-vibration excitation device 11. In other words, the micro-vibration excitation device 11 may change direction synchronously or not according to the steering device during enabling the crystalline silicon product B to generate plural times of the micro-vibrations, so as to increase detection accuracy.

Furthermore, when the fastening device 10 of the disclosure is the vacuum suction device, as illustrated in FIG. 1D and FIG. 1E, the steering device of the disclosure may be used to rotate the fastening device 10 of the disclosure to thereby change the direction.

Figure 5:
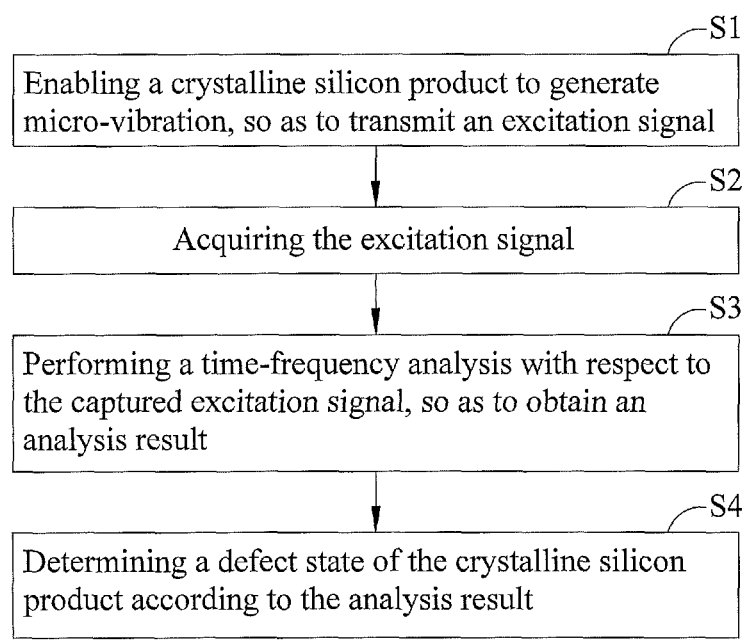
FIG. 5 is a step flow chart of a defect detection method in accordance with the disclosure.

Please refer to FIG. 5 illustrating a step flow chart of a defect detection method for detecting a crystalline silicon product in accordance with the disclosure.

In step S1, it enables a crystalline silicon product to generate micro-vibration, so as to generate a excitation signal from it, then proceeds to step S2. In the embodiment of step S1, it may also enable the crystalline silicon product to generate more than once micro-vibration with different direction in a predetermined time, so as to enable the crystalline silicon product to generate plural times of excitation signals in the predetermined time.

In step S2, the excitation signal is acquired. Next, step S3 is performed. In the embodiment of step S2, the excitation signal may be acquired by an industry-specific microphone including signal amplifier circuits and filtering circuits, while the acquired excitation signal may be further recorded during step S2.

In step S3, a time-frequency analysis is performed by a specific analysis with respect to the acquired excitation signal, so as to obtain analysis result. Next, step S4 is executed. In the illustrative embodiment of step S3, it may collectively analyze the acquired excitation signal in the time domain and the frequency domain by a short-time Fourier transform method, a continuous wavelet transform method, and/or a Hilbert-Huang transform approach, so as to obtain time, frequency, and energy change results of the excitation signal.

In step S4, a defect state of the crystalline silicon product is further determined according to the analysis result of step S3.

In an implementation aspect of the illustrative embodiment of step S4, the time-, frequency-, and energy-change results of the excitation signal may be characterized by a gridding method, then the characterized change results are analyzed by an artificial intelligence algorithm, so as to determine a defect state of the crystalline silicon product. That is, the time-, frequency-, and energy-change results of the excitation signal may be performed in a grid form by a smart processing equipment, then the gridding-performed change results are analyzed by an artificial neural network and/or a support vector machine, so as to determine the defect state of the crystalline silicon product.

In another aspect of the embodiment of step S4, the defect state of the crystalline silicon product is also determined by a visual-manual analysis according to whether or not related pulse surges present in the time-, frequency-, and energy-change results of the excitation signal. In other words, whether or not the related pulse surges are present in the time-, frequency-, and energy-change results of the excitation signal, is determined by the visual-manual analysis. And the analysis further determines whether the crystalline silicon product has fragmentation defects in case of the pulse surges being observed.

Additionally, the defect detection method of the disclosure may further carry out step S5 (not shown) after step S4 is performed. In step S5, the defect state determined in step S4 is displayed for relational inspectors to observe. The defect detection method of the disclosure may just perform steps S1 to S3 according to the need of the inspectors.

The detailed content of the short-time Fourier transform method, the continuous wavelet transform method, and/or the Hilbert-Huang transform approach mentioned in the disclosure may be referred to papers of "The empirical mode decomposition and the Hilbert spectrum for nonlinear and non-stationary time series analysis" published in The Royal Society, "Misalignment diagnosis of rotating machinery through vibration analysis via the hybrid EEMN and EMD approach" published in IOPscience, and "Vibration analysis of a cracked rotor using Hilbert-Huang transform" published in ScienceDirect.

In conclusion, the defect detection system and method of the disclosure enable the crystalline silicon product to generate the micro-vibration by the micro-vibration excitation device, so as to generate the excitation signal, then to acquire the excitation signal by the acquisition device, so as to analyze the excitation signal acquired by the acquisition device in the time and frequency domain by the analysis detection device with the specific analysis, and to obtain the analysis result, further enable the analysis detection device to determine the defect state of the crystalline silicon product generating the excitation signal according to the analysis result. Accordingly, the defect detection system and method of the disclosure not only can simultaneously and accurately detect the external fragmentation defects and the internal fragmentation defects of the crystalline silicon product, but also cause no improper damage to the tested crystalline silicon product and need no additional database, so as to reduce manufacturing cost.

The foregoing descriptions of the detailed embodiments are only illustrated to disclose the features and functions of the disclosure and not restrictive of the scope of the disclosure. It should be understood to those in the art that all modifications and variations according to the spirit and principle in the disclosure of the disclosure should fall within the scope of the appended claims.

What is claimed is:

1. A defect detection method for detecting a crystalline silicon product, comprising the steps of:
   (a) enabling, in a non-contact manner, the crystalline silicon product to generate micro-vibration, so as to generate an excitation signal;
   (b) acquiring the excitation signal generated from the crystalline silicon product by using an acquisition device; and
   (c) performing a time-frequency analysis with respect to the acquired excitation signal, so as to generate an analysis result,
   wherein step (a) enables the crystalline silicon product to generate more than once micro-vibrations with different directions in a predetermined time by changing direction of the crystalline silicon product, so as to enable the crystalline silicon product to generate the excitation signal in the predetermined time, and step (a) enables the crystalline silicon product to generate the more than once micro-vibrations at a side surface thereof.

2. The defect detection method of claim 1, further comprising a step (d) of determining a defect state of the crystalline silicon product according to the analysis result.

3. The defect detection method of claim 2, wherein in step (c) the time-frequency analysis is performed by a short-time Fourier transform method, a continuous wavelet transform method, or a Hilbert-Huang transform approach with respect to the acquired excitation signal, so as to obtain time-, frequency-, and energy-change results of the excitation signal; and in step (d) the defect state which comprises judgment of defect size, defect position, defect quantity, and/or defect alignment of the crystalline silicon product, is determined according to whether or not pulse surges are present in the time-frequency-, and energy-change results of the excitation signal.

4. The defect detection method of claim 3, wherein step (d) is performed to characterize the time-, frequency-, and energy-change results of the excitation signal and to analyze the change results by an artificial intelligence algorithm, so as to determine the defect state of the crystalline silicon product.

5. The defect detection method of claim 4, wherein the step of characterizing the time-, frequency-, and energy-change results of the excitation signal is performed in a grid form.

6. The defect detection method of claim 1, wherein step (b) further comprises recording the acquired excitation signal.

7. The defect detection method of claim 1, wherein in step (c) the time-frequency analysis is performed by a short-time Fourier transform method, a continuous wavelet transform method, or a Hilbert-Huang transform approach with respect to the acquired excitation signal, so as to obtain time-, frequency-, and energy-change results of the excitation signal.

8. The defect detection method of claim 1, further comprising a step (e) of displaying the defect state by a specific device.

9. A defect detection system for detecting a crystalline silicon product, comprising:
   a fastening device for fastening the crystalline silicon product;
   a micro-vibration excitation device for enabling, in a non-contact manner, the fastened crystalline silicon product to generate micro-vibration, so as to enable the crystalline silicon product to generate an excitation signal;
   an acquisition device for acquiring the excitation signal;
   an analysis detection device for performing a time-frequency analysis with respect to the acquired excitation signal by a specific analysis, so as to generate an analysis result; and
   a steering device for performing direction change with respect to the micro-vibration excitation device, wherein the micro-vibration excitation device enables the fastened crystalline silicon product to generate more than once micro-vibrations with different directions by changing direction of the crystalline silicon product using the steering device in a predetermined time, so as to generate the excitation signal,
   wherein the micro-vibration excitation device enables the fastened crystalline silicon product to generate the more than once micro-vibrations at a side surface thereof.

10. The defect detection system of claim 9, further comprising an isolation device for isolating the fastening device, the micro-vibration excitation device, and the acquisition device, so as to enable the acquisition device to acquire the excitation signal under no interference or low interference environment.

11. The defect detection system of claim 9, further comprising a display device for displaying a defect state of the crystalline silicon product.

12. The defect detection system of claim 9, wherein the analysis detection device further comprises a record module for recording the excitation signal acquired by the acquisition device and/or the analysis result generated by the analysis detection device.

13. The defect detection system of claim 9, wherein the analysis detection device performs a time-frequency analysis by a short-time Fourier transform method, a continuous wavelet transform method, or a Hilbert-Huang transform approach with respect to the excitation signal acquired by the acquisition device, so as to obtain time-, frequency-, and energy-change results of the excitation signal.

14. The defect detection system of claim 13, wherein the analysis detection device further characterizes the time-, frequency-, and energy-change results of the excitation signal by a gridding method, and analyzes the change results by an artificial intelligence algorithm, so as to determine a defect state of the crystalline silicon product.

15. The defect detection system of claim 9, wherein the fastening device comprises a clamping member and/or a suction member, so as to hold the crystalline silicon product by the clamping member and/or the suction member.

16. The defect detection system of claim 9, wherein the crystalline silicon product is a thin substrate.

17. The defect detection system of claim 9, wherein the excitation signal is a vibration signal.

18. The defect detection system of claim 9, wherein the analysis detection device further determines a defect state of the crystalline silicon product according to the analysis result.

* * * * *